United States Patent [19]

Lavretskaya et al.

[11] Patent Number: 4,735,953
[45] Date of Patent: Apr. 5, 1988

[54] PHARMACEUTICAL PREPARATION FOR LEARNING STIMULATION AND MEMORY IMPROVEMENT

[76] Inventors: Elionora F. Lavretskaya, Azovskaya ulitsa, 4, kv. 223, Moscow; Alexandra V. Upadysheva, ulitza Rozy Ljuxemburg, 4, kv. 59, Khimki; Anna P. Znamenskaya, Rizhsky proezd, 7, kv. 21, Moscow; Svetlana A. Sukhanova, ulitsa generala Dementieva, 7, kv. 63, Monino; Natalya D. Grigorieva, prospekt Mira, 24, kv. 10, Moscow; Ilmar K. Penke, ulitsa Lenina, 313, kv. 67, Riga; Alla K. Timofeeva, ulitsa Lenina, 30, kv. 18, Olaine, all of U.S.S.R.

[21] Appl. No.: 19,486

[22] Filed: Feb. 26, 1987

[30] Foreign Application Priority Data

Jul. 1, 1986 [SU] U.S.S.R. .................................. 4076765

[51] Int. Cl.$^4$ ............................................. A61K 31/47
[52] U.S. Cl. ..................................................... 514/313
[58] Field of Search .......................................... 514/313

[56] References Cited

U.S. PATENT DOCUMENTS 4,550,113 10/1985 Lavretskaya et al. ............. 514/290

Primary Examiner—Stanley J. Friedman
Attorney, Agent, or Firm—Burgess, Ryan & Wayne

[57] ABSTRACT

A pharmaceutical preparation for learning stimulation and memory improvement comprising an active principle, viz. 9-amino-2,3,5,6,7,8-hexahydro-1H-cyclopenta(b)quinoline monohydrate hydrochloride of the following formula:

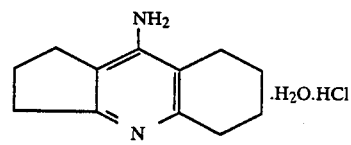

and a pharmaceutically-acceptable vehicle.

5 Claims, No Drawings

PHARMACEUTICAL PREPARATION FOR LEARNING STIMULATION AND MEMORY IMPROVEMENT

FIELD OF THE INVENTION

The present invention relates to the art of medicine and, more specifically, to a novel pharmaceutical preparation for stimulation of learning and improvement of memory which can be useful in the treatment of diseases accompanied by memory disorders and learning hindrances, in the case of dementia of the Alzheimer and Pick type, senile dementia and that of a vascular origin, as well as for the treatment of children and youngsters suffering from various forms of an organic injury of brain, such as minimum brain disfunction.

BACKGROUND OF THE INVENTION

An increase in the average human lifespan during recent decades and the growing percentage of people of elderly and senile age have resulted in a greater number of diseases of the elderly, including those accompanied by memory disturbances.

The latter can be exemplified by such varieties of memory disorders as vascular dementia (atherosclerotic brain injury), senile dementia, as well as Alzheimer and Pick's dementia.

Effective preparations which would provide a pronounced therapeutic effect on these categories of patients have been hitherto unknown in the art. For the treatment of vascular dementia use is made primarily of vasodilating agents, preparations improving brain metabolism and blood flow. In the case of atrophic processes—senile dementia, Alzheimer and Pick's disease no groups of preparations provide any noticeable effect. The theory of injury of the cholinergic transmission in the case of Alzheimer's disease has resulted in attempts of use, for therapeutical purposes, cholinomimetics, acetylcholine precursors and choline-esterase inhibitors. To date, these efforts, however, failed to be successful.

At the present time, used for memory improvement in the case of these forms of pathology are such preparations as nootropyl (pyracetam), calcium salt of homopantothenic acid (pantogam); whereas administered for the treatment of Alzheimer's disease are certain choline-esterase inhibitors, such as physostigmine (Biological Psychiatry, vol. 16, No. 2, 1981, p. 145–153; Biological Psychiatry, vol. 17, No. 2, 1982, pp. 275–280; Pharmakologiya i Toxicologiya, "Meditsina" Publishing House, Moscow, 1973, No. 4, p. 483–494).

Known in the art is a compound, viz. 9-amino-2,3,5,6,7,8-hexahydro-1H-cyclopenta-(b)quinoline monohydrate hydrochloride which is useful as an active principle of a pharmaceutical preparation for stimulation of neuro-muscular transmission, smooth muscles, and propagation of excitation in the peripheral and central nervous system (cf. U.S. Pat. No. 4,550,113, 1985, Int. Cl.

However, the use of this pharmaceutical preparation as an active principle of a composition for learning stimulation and memory improvement is unknown in the art.

All these preparations feature but an insufficient effectiveness and do not result in complete restoration of memory.

SUMMARY OF THE INVENTION

It is an object of the present invention to provide a novel pharmaceutical preparation for stimulation of learning and memory improvement which would have a novel mechanism of action on the brain functions and feature a high efficiency and low toxicity.

The preparation according to the present invention is novel and hitherto has not been described in the literature.

The object of the present invention is accomplished by providing a pharmaceutical preparation for learning stimulation and memory improvement comprising an active principle and a pharmaceutically acceptable vehicle containing, according to the present invention, as the active principle 9-amino-2,3,5,6,7,8-hexahydro-1H-cyclopenta(b)quinoline monohydrate hydrochloride of the following formula:

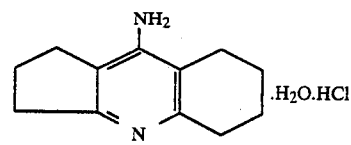

The pharmaceutical preparation according to the present invention can be used in different pharmaceutical forms. It is preferable to use it as an injectable solution and tablets. The pharmaceutical preparation according to the present invention in the form of an injectable solution preferably contains the active principle in an amount of from 0.5 to 1.5% by weight, while as the pharmaceutically acceptable vehicle it preferably contains a solvent—bidistilled water acidified to the pH of 3.0. The pharmaceutical preparation according to the present invention in the form of tablets preferably contains the active principle in an amount of from 10 to 20 mg per one tablet. As the pharmaceutically acceptable vehicle it contains a filler for tablets, preferably starch, sugar powder.

The pharmacological activity of the preparation according to the present invention has been tested in experiments on animals and clinically on humans suffering from brain diseases accompanied by memory disorders.

DETAILED DESCRIPTION OF THE INVENTION

The pharmaceutical preparation according to the present invention has been tested on male rats with a mass of 180–220 g, male mice with a mass of 30–40 g aged 12 weeks and on rabbits with a mass of 2.5–3 kg.

In the first series of experiments there was studied the effect of the preparation according to the present invention on education of rats in a "shuttle" chamber with the dimensions of 36×18×19 cm using the active avoidance method. In these experiments rats are taught to avoid an electric shock by escaping into a next chamber communicating with the first chamber by means of a special opening—a door. An electric current is applied to the chamber door consisting of metal plates. A conditional irritator is a light signal together with a sound click. The learning series consisted of 50 combinations. The number of combinations necessary for the animal's learning to escape into another chamber in response to the conditional signal was determined. Five correct responses out of 6 where regarded as the proof of stability of the acquired knowledge and were denoted as a "learning criterion". After 7 days the educational procedure was repeated, and again the number of combinations necessary to acquire the "learning criterion" was determined. In the case of difference between the first and second readings the percentage of retention of the acquired knowledge was calculated.

In this experiment the effect of the preparation according to the present invention and prior art preparations was separately evaluated for the purpose of comparison on well-learning and on specially selected poorly learning rats. The experiment demonstrated a different effect of some preparations on these groups of animals. To the poorly learning rats the animals were assigned which reached no "learning criterion" in the teaching series of 50 combinations, or, in other words, a stable knowledge of active avoidance was not worked out in them. The well-learning animals reached the "learning criterion" after 15–25 combinations. The preparation according to the present invention and the prior art comparison preparations were administered before the first teaching series or thereafter.

As the comparison preparations use was made of pyracetam, physostigmine, 4-aminopyridine, calcium homopantathenate, lysyl-vasopressin; as the control a physiological solution was used.

Also studied were the effects produced upon a single and repeated administration of the preparation according to the present invention for 14 days.

In the second series of experiments the preparation according to the present invention was studied for the effect on teaching of rats in a T-shaped labyrinth in one compartment of which a feedbox with meal was provided. Rats deprived of meals during the day were placed into the starting compartment of the labyrinth and taught to find the feed-box in the proper compartment of the labyrinth. The response time, the number of unrealized reactions, the latent period, and the number of errors were noted.

In the third series of experiments the effect of the preparation according to the present invention on the functional brain asymmetry was studied. The experiments were carried out on rabbits with electrodes implanted in the brain. The electrodes under nembutal narcosis (40 mg/kg) were implanted strictly symmetrically into the bearing zone of the temporal cortex of the right and left hemispheres on its lateral surface, whereas the indifferent electrode was secured to the nasal bones of a rabbit's skull. The acoustic irritation was applied through earphones. As the acoustic irritation a sound click caused by a square-shaped pulse from an electronic stimulator with a frequency of 0.1–0.2 Hz was used; the click intensity was adjusted within the range of from 5 to 80 Db. The amplification of the taken-off biopotentials was effected on an electroencephalograph; the induced potentials were obtained by means of an analyzer. 100 experiments on 20 animals were thus conducted; the interval between experiments on one animal was 7 days. The amplitude and form of the induced potential were determined. The asymmetry factor ($K_{as}$) was calculated by the formula:

$$K_{as} = \frac{A_r - A_l}{A_r + A_l}, \text{ wherein:}$$

$A_r$—amplitude of the induced potential of the left hemisphere, $\mu V$;

$A_l$—amplitude of the induced potential of the left hemisphere.

The test preparations were administered hypodermally in the form of 0.5–1.5% aqueous solutions 20 minutes before the beginning of the measurements.

Also studied was the change of lateralization of free behaviour of rats in the T-shaped labyrinth. In the experiment rats of both sexes with a mass of 180–230 g were used. Preliminary experiments were carried out on 120 animals, then a group of 40 animals was chosen which during 20 days selected the left corridor in the first attempt of running through the labyrinth.

In the first series of experiments the preparation according to the present invention was found to stimulate the learning capacity of rats when administered in the doses of 1, 5 and 10 mg/kg. This resulted in a reduced number of combinations required for the formation of the "learning criterion". The test results are shown in Table 1 hereinbelow. It should be noted that the pharmaceutical preparation according to the present invention exerts and influence not only on the learning process, but also on retention of the obtained knowledge, i.e. on the memory itself. Especially pronounced is the effect of the proposed preparation on the rats which have been previously less susceptible to the teaching process and kept out of experimental sorting. After two-weeks of administration of the preparation according to the present invention its stimulating effect is also enhanced as compared to a single-time administration. The results of these tests are shown in Table 2 hereinbelow. As best seen in Tables 1 and 2, the pharmaceutical preparation according to the present invention used in these experiments has been substantially more active than 4-aminopyridine, physostigmine, pyracetam and lysyl-vasopressin.

Similar results were obtained in experiments in a T-shaped labyrinth with the use of a positive meal support. In rats preliminarily treated with the preparation according to the present invention in the doses of 1, 5 and 10 mg/kg there is evidenced a reduced number of response failures. Thus, when administered in the dose of 5 mg/kg, the preparation according to the present invention reduced the number of response failures by the fourth day of teaching to 40% as compared to the initial level on the first day of teaching, whereas in the control this figure remained at the level of 60–70%.

In the third series of experiments it was shown that the pharmaceutical preparation according to the present invention provides an effect on induced audibility potentials in the cerebral cortex of rabbits and amplifies the activity of the left hemisphere. The results of corresponding tests are shown in Table 3 hereinbelow. The amplitude of induced potentials is increased greater in the left hemisphere; the asymmetry factor is also increased. No other out of the tested preparations revealed such effect. Pyracetam (nootropyl) failed to influence all these characteristics, whereas 4-aminopyridine and physostigmin increased amplitude of the induced potential, but did not change or reduced the factor of asymmetry. The test results are shown in Table 4 hereinbelow.

TABLE 1

Effect of the preparation according to the present invention and comparison preparations on the learning ability of rats in a shuttle chamber

| Nos 1 | Preparation dose, mg/kg 2 | Number of animals 3 | Number of combinations to reach the "learning criterion" in the I teaching series 4 | Number of combinations to reach the "learning criterion" in II teaching series (after 7 days) 5 | Percentage of knowledge retention 6 | Number of non-taught animals in the group 7 |
|---|---|---|---|---|---|---|
| 1 | Control, preparation of the invention, hypodermally | 30 | 20.6 + 2.2 | 8.9 + 1.05 | 56.8 | 6/30 |
| 2 | 1 mg/kg | 20 | 14.2 + 1.2$^x$ | 4.2 + 0.8$^{xxx}$ | 70.4 | 3/20 |
| 3 | 5 mg/kg | 20 | 11.5 + 0.9$^{xxx}$ | 2.6 + 0.3$^{xxx}$ | 77.4 | 1/20 |
| 4 | 10 mg/kg | 15 | 12.9 + 0.8$^{xx}$ | 3.0 + 0.5$^{xxx}$ | 76.7 | 0/15 |
| 5 | Control, preparation of the invention 5 mg/kg, per os | 20 20 | 25.3 + 3.6 12.8 + 1.7$^{xxx}$ | 7.9 + 1.2 6.0 + 0.5 | 64.9 60 | 5/20 2/20 |
| 7 | Control, preparation of the invention, hypodermally 5 mg/kg after teaching | 10 20 | 19.8 ± 1.5 19.0 ± 1.2$^{xx}$ | 10.2 ± 1.2 7.2 ± 0.8$^x$ | 48.5 60 | 2/10 1/20 |
| 9 | Control preparation of the invention, hypodermally | 10 | 19.3 ± 2.7 | 6.6 ± 0.9 | 66 | 2/10 |
| 10 | 1 mg/kg 14 days | 20 | 14.7 ± 1.9 | 3.9 ± 0.8$^x$ | 72.7 | 2/20 |
| 11 | 5 mg/kg, hypodermally 14 days | 20 | 14.8 ± 2.0 | 4.4 ± 0.5$^x$ | 69.3 | 2/20 |
| 12 | Control 4-aminopyridine | 10 | 25.5 ± 2.5 | 9.5 ± 0.9 | 62.6 | 1/10 |
| 13 | 2 mg/kg hypodermally | 20 | 17.8 ± 1.2$^{xx}$ | 7.4 ± 1.2 | 60 | 0/20 |
| 14 | Control | 10 | 24.8 ± 2.8 | 7.2 ± 1.1 | 70 | 2/10 |
| 15 | Physostigmine, 0.04 mg/kg hypodermally | 20 | 21.9 ± 2.5 | 6.1 ± 0.9 | 72 | 1/20 |
| 16 | Pyracetam 100 mg/kg hypodermally | 20 | 20.8 ± 1.2 | 4.7 ± 0.9 | 70 | 1/20 |
| 17 | Lysyl-vasopressin, 20 g/kg hypodermally | 20 | 14.2 ± 1.5$^{xxx}$ | 4.2 ± 0.5$^{xx}$ | 70 | 0/20 |

$^x$P < 0.05
$^{xx}$P < 0.02
$^{xxx}$< 0.002

TABLE 2

Effect of the preparation according to the present invention on the learning ability of rats preliminarily sorted out for poor learning ability

| Nos 1 | Preparation 2 | Dose mg/kg hypodermally 3 | Number of animals 4 | Number of combinations till appearance of "learning criterion" | | % of knowledge retention 7 | Number of untaught animals in the group 8 |
|---|---|---|---|---|---|---|---|
| | | | | I teaching 5 | II-checking retention of knowledge 6 | | |
| 1 | Control | — | 20 | 6 ± 1.9 | 42 ± 2.4 | 8.7 | 15/20 |
| 2 | Preparation of the invention | 1 | 20 | 24 ± 2.5$^x$ | 10.2 ± 1.5 | 57.5 | 6/20 |
| 3 | | 5 | 20 | 21 ± 2.7$^x$ | 7.5 ± 0.9 | 64.3 | 3/20 |
| 4 | Control | — | 20 | 44 ± 2.9 | 40 ± 3.5 | | 15/20 |
| 5 | 4-aminopyridine | 2 | 20 | 32.5 ± 2.8$^x$ | 19.2 ± 1.7 | 40.9 | 11/20 |
| 6 | Physostigmine | 0.04 | 20 | 46 ± 3.1 | 31.4 ± 1.8 | 10 | 12/20 |
| 7 | Pyracetam | 100 | 20 | 30.3 ± 2.5$^x$ | 22.4 ± 2.1 | 26 | 9/20 |

$^x$the difference with the control is statistically verified, p < 0.05

TABLE 3

Effect of the preparation according to the present invention and of other preparations on amplitude of induced potential in rabbit's brain hemispheres

| Preparation | Dose, mg/kg hypodermally | Change of amplitude of induced potential, % of the control | | Mean value of amplitude of induced potential, % |
|---|---|---|---|---|
| | | left hemisphere | right hemisphere | |
| Preparation of the invention | 5 | 270 | 200 | 235 |
| 4-aminopyridine | 2 | 140 | 175 | 160 |
| Physostigmine | 0.04 | 115 | 175 | 145 |
| Galantamine | 3 | 150 | 165 | 160 |
| Pyracetam | 100 | 110 | 105 | 107 |

TABLE 4

Effect of the preparation according to the present invention and of other preparations on asymmetry factor by values of the induced potential in the hearing zone of the cerebral cortex of rabbits

| Preparation | Dose, mg/kg hypodermally | Number of animals | Asymmetry factor | |
|---|---|---|---|---|
| | | | Control | Preparation |
| Preparation of the invention | 5 | 8 | 0.18 ± 0.05 | 0.29 ± 0.07 |
| 4-aminopyridine | 2 | 6 | 0.26 ± 0.06 | 0.12 ± 0.02 |
| Physostigmine | 0.04 | 6 | 0.22 ± 0.01 | 0.11 ± 0.01 |
| Galantamine | 3 | 6 | 0.26 ± 0.03 | 0.19 ± 0.03 |
| Pyracetam | 100 | 10 | 0.19 ± 0.03 | 0.213 ± 0.05 |

The data on the capacity of the preparation according to the present invention to enhance the domination of one (left) brain hemisphere have been supported in behaviour experiments on rats where the change in lateralization of a free behaviour of rats in a T-shaped labyrinth was studied. When the rats persistently, choosing the left side of the labyrinth in the first running-through were selected, after administration of the preparation according to the present invention to them the choice of the right side of the labyrinth by them was statistically markedly increased. The test results are shown in Table 5 hereinbelow.

TABLE 5

Effect of the preparation according to the present invention on lateralization of free behaviour of rats persistently choosing the left side of the labyrinth

| Preparation | Dose, kg/mg hypodermally | Number of animals | Number of runs to the right | | |
|---|---|---|---|---|---|
| | | | Series I | Series II | Series III |
| Control | — | 40 | 0 | 2 | 3 |
| Preparation of this invention | 5 | 20 | 10 | 12 | 14 |
| Preparation of this invention | 10 | 20 | 9 | 14 | 15 |

The results of experiments on mice aged 12 weeks have shown that in these animals the preparation according to the present invention in the doses of 1, 3 and 10 mg/kg facilitates the learning process during the first day of teaching and improves retention of the acquired knowledge upon checking after 24 hours. In doing so, the preparation according to the present invention is more efficient than pyracetam, 4-aminopyridine, physostigmine and calcium homopantothenate. The results of the tests are shown in Table 6 hereinbelow.

Upon comparison of various routes of administration of the preparation according to the present invention it has been shown that its administration per os provides the same or even better results of memory stimulation as compared to its subcutaneous administration. 4-aminopyridine facilitates teaching, but does not affect the retention of the knowledge of active avoidance. Physostigmine in the dose of 0.03 mg/kg slightly improves and in the dose of 0.1 mg/kg impairs teaching of animals. Pyracetam, when administered hypodermally, improves learning, but not memory; upon its administration per os the effect is noticeably reduced. Calcium homopantothenate provides an improving effect on learning only in a high dose—100 mg/kg, the hypodermal administration of this preparation provides a substantially more pronounced effect than its per os administration.

The preparation according to the present invention was also tested for acute and chronic toxicity.

The $LD_{50}$ upon single intraperitoneal administration to mice was 44 mg:/kg; hypodermally—52 mg/kg, per os—68 mg/kg; hypodermally to rats—60 mg/kg.

The chronic toxicity of the preparation was studied on three species of animals (rats, dogs, rabbits). In chronic tests on the above-mentioned animals the effect of a long-time hypodermal administration of the preparation according to the present invention on the general state and mass of animals, hemogram, cardio-vascular system, breathing central nervous system, functional state of kidneys, liver, thyroid gland was studied. On the basis of the obtained results and morphological investigations it has been found that the preparation according to the present invention in a lasting treatment course (rats—3 months, rabbits—2 months, dogs—6 months) provides no toxic effect on the laboratory animals. The doses of the preparation employed in the experiments surpassed the required dose for a human being (per kilogram of bodymass) by 5-10 times.

Allergenic activity tests were also carried out for the preparation according to the present invention. The test results have shown that the preparation of this invention provided no allergenic effect.

The preparation according to the present invention neither provides a carcinogenic, mutagenic, teratogenic or embryotoxic effect.

TABLE 6

Effect of the preparation according to the present invention as compared to the prior art preparations on the learning ability of mice (aged 12 weeks, mass 30–40 g) in a shuttle chamber

| Nos 1 | Preparation 2 | Dose, mg/kg 3 | Route of administration 4 | Number of animals 5 | % of avoidance reactions in 6 groups of experiments (20 tests in each) 1-st-day of teaching | | | | | | % of avoidance reactions in 6 groups of experiments (20 tests in each 12 day of teaching (retention of knowledge) | | | | | |
|---|---|---|---|---|---|---|---|---|---|---|---|---|---|---|---|---|
| | | | | | I 6 | II 7 | III 8 | IV 9 | V 10 | VI 11 | I 12 | II 13 | III 14 | IV 15 | V 16 | VI 17 |
| 1 | Control | — | — | 39 | 20 | 21 | 26 | 35 | 40 | 42 | 52 | 67 | 72 | 76 | 80 | 82 |
| 2 | Preparation of the invention | 1 | hypodermally | 20 | 22 | 40 | 52 | 60 | 70 | 74 | 70 | 88 | 90 | 90 | 91 | 90 |
| 3 | | 3 | " | 20 | 32 | 43 | 50 | 61 | 67 | 65 | 66 | 90 | 88 | 87 | 86 | 86 |
| 4 | | 10 | " | 20 | 28 | 20 | 25 | 40 | 44 | 46 | 61 | 75 | 78 | 77 | 76 | 81 |
| 5 | Control | — | — | 30 | 20 | 23 | 41 | 44 | 53 | 50 | 53 | 79 | 80 | 81 | 82 | 80 |
| 6 | preparation of this invention | 0.3 | per os | 20 | 27 | 38 | 59 | 65 | 68 | 72 | 79 | 84 | 82 | 83 | 80 | 82 |
| 7 | | 1 | per os | 20 | 27 | 43 | 70 | 80 | 80 | 82 | 80 | 90 | 88 | 87 | 86 | 90 |
| 8 | | 3 | per os | 30 | 18 | 27 | 35 | 44 | 51 | 50 | 51 | 76 | 75 | 77 | 79 | 80 |
| 9 | Control | — | — | 39 | 21 | 22 | 27 | 37 | 41 | 45 | 50 | 68 | 72 | 75 | 80 | 81 |
| 10 | 4-aminopyridine | 1 | hypodermally | 20 | 17 | 21 | 38 | 51 | 55 | 60 | 48 | 70 | 72 | 71 | 70 | 75 |
| 11 | | 3 | " | 20 | 20 | 30 | 54 | 61 | 79 | 82 | 46 | 73 | 74 | 74 | 80 | 80 |
| 12 | Control | — | — | 39 | 20 | 22 | 25 | 34 | 40 | 43 | 51 | 62 | 70 | 72 | 80 | 81 |
| 13 | Physostigmine | 0.03 | " | 20 | 20 | 21 | 26 | 35 | 49 | 57 | 50 | 80 | 83 | 87 | 90 | 89 |
| 14 | | 0.1 | " | 20 | 18 | 4 | 7 | 18 | 23 | 38 | 39 | 60 | 70 | 70 | 71 | 70 |
| 15 | Control | — | — | 39 | 22 | 23 | 25 | 39 | 42 | 45 | 51 | 68 | 72 | 75 | 76 | 78 |
| 16 | Pyracetam | 10 | hypodermally | 20 | 23 | 33 | 48 | 52 | 60 | 61 | 60 | 78 | 80 | 79 | 80 | 78 |
| 17 | | 30 | " | 20 | 20 | 32 | 55 | 67 | 70 | 75 | 60 | 80 | 82 | 81 | 84 | 88 |
| 18 | | 100 | " | 20 | 24 | 41 | 55 | 70 | 72 | 74 | 62 | 90 | 92 | 90 | 90 | 92 |
| 19 | Control | — | — | 39 | 20 | 22 | 24 | 35 | 40 | 45 | 46 | 66 | 70 | 72 | 78 | 79 |
| 20 | Calcium homopantothenate | 30 | hypodermally | 20 | 21 | 23 | 40 | 55 | 58 | 60 | 55 | 80 | 82 | 85 | 84 | 88 |
| 21 | | 100 | " | 20 | 20 | 31 | 40 | 55 | 58 | 60 | 60 | 90 | 90 | 89 | 90 | 88 |
| 22 | | 300 | " | 20 | 21 | 32 | 40 | 50 | 51 | 55 | 53 | 75 | 76 | 76 | 74 | 74 |
| 23 | Control | — | — | 30 | 19 | 26 | 40 | 48 | 52 | 50 | 54 | 73 | 74 | 75 | 82 | 82 |
| 24 | Pyracetam | 30 | per os | 20 | 11 | 17 | 31 | 32 | 33 | 40 | 48 | 70 | 71 | 78 | 78 | 81 |
| 25 | | 100 | per os | 20 | 21 | 22 | 32 | 42 | 43 | 52 | 69 | 80 | 82 | 79 | 78 | 78 |
| 26 | Calcium homopantothenate | 300 | per os | 20 | 21 | 22 | 32 | 42 | 43 | 51 | 50 | 72 | 73 | 78 | 77 | 80 |

The preparation according to the present invention was studied in clinics on 130 patients.

As regards diagnosis and sex the patients were distributed as follows:
- skull-brain traumata with memory disturbance: 75 patients (52 men and 23 women)
- Alzheimer's disease: 15 patients (3 men and 12 women)
- Pick's disease: 5 patients (5 men)
- Senile dementia: 15 patients (4 men and 11 women)
- Vascular dementia (cerebral atero-sclerosis, hypertonic disease): 20 patients (7 men and 13 women)

In the group of patients with skull-brain trauma the patient's age varied from 17 to 60 years, in the other patients—from 52 to 75 years.

In addition to clinico-psychopathological methods of investigation, all the patients were subjected to neuropsychological studies during which specific tasks were offered them to solve. In doing so, the response was assessed against a 4-points scale: 3—maximally pronounced disorder, full or substantially full incapability to deal with the task set; 2—a medium degree of manifestation of the deficiency, solving the task with the experimentator's assistance; 1—minor errors, independent correction of mistakes; 0—lack of disturbances.

All the patients were administered the preparation according to the present invention in doses ranging from 5 to 30 mg a day in the form of subcutaneous injections, or with pyracetam (a 20% solution) by injections of 5 ml intramuscularly (90 and 40 patients in each group respectively). The treatment course duration is 30–60 days. In the case of an acute skull-brain trauma (65 patients) the treatment started 15–20 days after the moment of trauma and lasted for 20–30 days.

The results of the treatment performed point to a high therapeutic effect of the preparation according to the present invention and its advantages over the prior art preparation—pyracetam:

by the moment of the treatment beginning in both groups considerable disturbances of psychic functions were observed, as regards the severity and character of memory disorders no substantial difference was noticed in both groups. By the end of the treatment course a considerable regression of all disturbances or diminution of their severity was observed. However, a faster and more complete restoration of psychic functions took place in the case of administration of the preparation according to the present invention as compared to pyracetam.

These two groups of patients differed not only in the rate of recovery of memory and praxis, but in the character of this recovery. Pyracetam resulted in a uniform regression of all available disorders, whereas the preparation according to the present invention exhibited selectivity of its action. Under its influence the constructive and environmental praxis recovered most efficiently along with reading ability and memory.

The preparation according to the present invention provided a non-uniform effect on different parameters of the same function. Especially clearly this was pronounced in a neuropsychological study of memory functions.

It is known that the function of memory has a complex brain organization and different zones of brains take part in its regulation. During the studies a multifaceted assessment of the memory function was carried out; there were assessed: (1) mnestic component of the environmental orientation of a patient; (2) involuntary memory for current events; (3) intentional exo-experimental memory; (4) volume and soundness of audio-speaking memory; (5) volume and soundness of visual memory; (6) operative memory; (7) memory for knowledge acquired before the disease.

The preparation according to the present invention produced a more complete and faster recovering effect on the following memory parameters: mnestic component of the environmental orientation; strengthening of the past experience's knowledge; involuntary memory for current events; voluntary exo-experimental memory and operative memory. It should be noted that these parameters are of a special significance in a rapid social rehabilitation of patients. The visual memory recovered faster than the audio memory.

These data enable a conclusion that the pharmaceutical preparation according to the present invention exerts its primary effect on the posteroparietal zones of the left hemisphere.

Therefore, in both experimental and clinical studies the ability of the preparation according to the present invention to provide an effect on the functional symmetry of the brain and an enhanced activity of the dominating hemisphere have been revealed. Pyracetam has no such effect.

The preparation according to the present invention is the most effective in the case of an acute skull-brain trauma where it demonstrated a faster and more complete recovery of psychic functions. A good therapeutic effect was also provided by the preparation according to the present invention on patients with consequences of a vascular injury of brains; in this case an improvement of memory was noted along with a higher working capacity of a patient. An essential amelioration was noted in patients suffering from Alzheimer's and Pick's diseases.

The effect of the pharmaceutical preparation according to the present invention on learning and memory improvement is based on the effects at the molecular level combined in optimal proportions: block of potassium channels of the membrane and inhibition of choline-esterase which result in an increased liberation of neurotransmitters in all synapses, especially in cholinergic ones. This contributes to an enhanced efficiency of each nervous pulse in transmittance of information in the nervous system. Besides, the revealed effect of the preparation according to the present invention on the functional asymmetry of the brains with an enhanced domination of the left hemisphere can result in stimulation of a whole number of psychic functions, including memory.

The preparation according to the present invention is administered in various pharmaceutically acceptable forms: per os as tablets, capsules, syrup, pills, as injection solutions for hypodermal, intramuscular and intravenous administration; also as suppositoria. The preparation according to the present invention is administered in doses of from 5 to 20 mg 1-2 times a day. The treatment course is chosen on an individual basis and amounts to 20-60 days on the average. Treatment courses can be repeated for several times during a year with an interval of 1-2 months.

The preparation according to the present invention is well-bearable by patients. Among its side effects there have been noted signs of stimulation of m-cholinergic systems, namely; nausea, diarrhea, less frequently—vomition. In rare cases there is noticed reduction or elevation of arterial pressure and bradycardia which are eliminated by way of lowering the preparation dose or a temporary suspension of its administration. In cases of poisoning injections of atropine can be used.

Contraindications against the use of the pharmaceutical preparation according to the present invention are extrapyramide injuries of the nervous system with hyperkinesises, organic disturbances of the heart with bradycardia, bronchial asthma, epilepsy.

The pharmaceutical forms of the preparation according to the present invention are obtained by conventional methods. The active principle, namely: 9-amino-2,3,5,6,7,8-hexahydro-1H-cyclopenta(b)quinoline monohydrate hydrochloride should be preferably produced in the following manner.

1-Amino-2-cyanocyclopentene-1, cyclohexanone, polyphosphoric acid and dry benzene are intermixed at reflux for 2 hours. After cooling the reaction mass is diluted with water and extracted with ethyl ether. The ethereal extract is discarded. The aqueous layer is neutralized to the pH of 7. The resulting precipitate is filtered-off and washed with water for several times on the filter. After separation of the residue the aqueous layer is combined with washing waters and alkalinified with ammonia to a pH of 9-10. The formed precipitate of 9-amino-2,3,5,6,7,8-hexahydro-1H-cyclopenta(b)quinoline is filtered-off and washed, then dissolved in 20 ml of ethanol, whereafter gaseous hydrogen chloride is passed through the alcoholic solution at a temperature within the range of from 5° to 25° C. to the pH of 3. The resulting salt is precipitated by means of ethyl ether, the precipitate is resedimented from ethanol by ether to give 9-amino-2,3,5,6,7,8-hexahydro-1H-cyclopenta(b)quinoline monohydrate hydrochloride comprising a white or slightly creamy powder without odour, well soluble in water, less soluble in a 95% ethanol, substantially insoluble in acetone, ether, chloroform, readily soluble in diluted solutions of acids.

The pharmaceutical preparation according to the present invention pertains to the List B substances and should be kept in a light-protected place.

What is claimed is:

1. A method for learning stimulation and memory improvement which comprises administering to a mammal requiring such treatment a learning stimulation or memory improving amount of a pharmaceutical preparation containing from 0.5 to 1.5% by weight of 9-amino-2,3,5,6,7,8-hexahydro-1H-cyclopenta(b)quinoline monohydrate hydrochloride of the following formula:

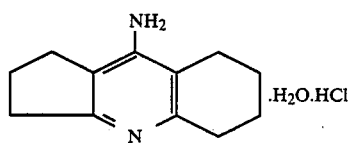

and a pharmaceutically-acceptable vehicle.

2. The method of claim 1, wherein the pharmaceutical preparation is in the form of an injectable solution.

3. The method of claim 1, wherein the pharmaceutical preparation contains as the pharmaceutically-acceptable vehicle, bidistilled water acidified to the pH of 3.0.

4. The method of claim 1, wherein the pharmaceutical preparation is in tablet from and contains the active principle in an amount ranging from 10 to 20 mg per tablet.

5. The method of claim 4, wherein the tablet contains a filler selected from the group consisting of starch and sugar powders.

* * * * *